(12) United States Patent
Okamoto et al.

(10) Patent No.: US 7,932,226 B2
(45) Date of Patent: Apr. 26, 2011

(54) NFκB TRANSCRIPTIONAL ACTIVITY INHIBITORY AGENT AND ANTI-INFLAMMATORY AGENT AND A STEROID ACTION ENHANCING AGENT

(75) Inventors: Kazuki Okamoto, Osaka (JP); Fumihide Isohashi, Osaka (JP)

(73) Assignee: St. Marianna University School of Medicine, Kawasaki-shi (JP)

( * ) Notice: Subject to any disclaimer, the term of this patent is extended or adjusted under 35 U.S.C. 154(b) by 802 days.

(21) Appl. No.: 11/631,202

(22) PCT Filed: Jun. 28, 2005

(86) PCT No.: PCT/JP2005/011851
§ 371 (c)(1),
(2), (4) Date: Dec. 7, 2007

(87) PCT Pub. No.: WO2006/001453
PCT Pub. Date: Jan. 5, 2006

(65) Prior Publication Data
US 2008/0287351 A1    Nov. 20, 2008

(30) Foreign Application Priority Data

Jun. 29, 2004    (JP) .................................. 2004-192160

(51) Int. Cl.
*A61K 38/16*    (2006.01)
*C07K 14/00*    (2006.01)
(52) U.S. Cl. ......................................... 514/12; 530/300
(58) Field of Classification Search .................. None
See application file for complete search history.

(56) References Cited

U.S. PATENT DOCUMENTS

| 6,780,970 B2 | 8/2004 | Bonny ........................ 530/324 |
| 2004/0002521 A1 | 1/2004 | Iino et al. ................... 514/344 |

FOREIGN PATENT DOCUMENTS

| JP | 8-319238 | 12/1996 |
| JP | 9-59151 | 3/1997 |
| JP | 11-279057 | 10/1999 |
| JP | 2000-224993 | 8/2000 |
| JP | 2003-511071 | 3/2003 |
| WO | WO 02/26547 | 5/2002 |
| WO | WO 02/36547 | 5/2002 |
| WO | WO 03/016475 | 2/2003 |
| WO | WO 03/072035 | 9/2003 |

OTHER PUBLICATIONS

Okamoto, et al., "The new type coactivator (MTI-ii) colocalizes with gulucocorticoid-receptor and enhances transcription through its acidic domain in vivo," *Seikagaku*, vo. 76, No. 8, p. 1046, Aug. 25, 2004.

Okamoto, et al., "The nuclear acidic protein (MTI-II is a new type of nuclear-receptor coactivator,"*Vitamins*, vol. 78, No. 4, p. 283, 2004.
Scheinman, et al., "Characterization of Mechanisms Involved in Transrepression of KF-fB by activated Glucocoriticoid Receptors," *Molecular and Cellular Biology*, Vo. 15, No. 2, p. 943-953, 1995.
International Search Report in PCT/JP2005/011851 dated Aug. 9, 2005.
Almawi et al., "Negative Regulation of Nuclear Factor-κB Activation and Function by Glucocorticoids,"*J. Mol. Endo.*, 28(2):69-78 (2002).
D'Acquisto et al., "Inhibition of Nuclear Factor Kappa B (NF-κB): An Emerging Theme in Anti-Inflammatory Therapies," *Mol. Interv.*, 2(1):22-35 (2002).
Hannappel et al., "The Thymosins. Prothymosin α, Parathymosin, and β-Thymosins: Structure and Function," *Vitamins and Hormones*, 66:257-296 (2003).
Leondiadis et al., "Synthesis, Mass Spectrometry Analysis and Potency of an Parathymosin (101 Amino Acids)," *J. Peptide Sci.*, 8(Supp.):S118 (2002).
Okamoto et al., "Macromolecular Translocation Inhibitor II ($Zn^{2+}$-Binding Protein, Parathymosin) Interacts with the Glucocorticoid Receptor and Enhances Transcription in Vivo," *J. Biol. Chem.*, 280(44):36986-36993 (2005).
Okamoto et al., "Purification and Primary Structure of a Macromolecular-Translocation Inhibitor II of Glucocorticoid-Receptor Binding to Nuclei from Rat Liver Inhibitor II is the 1 1.5-kDa $Zn^{2+}$-Binding Protein (Parathymosin)," *Eur. J. Biochem/FEBS*, 267(1):155-162 (2000).
Salvin et al., "Potential Regulation of Immunity by the Peptides Prothymosin α and Parathymosin," *Lymphokine Res.*, 6(1):1437 (1987).
Salvin et al., "Regulation of Immune Responses by the Thymic Peptides, Prothymosin-α and Parathymosin-$α^1$," *Natural Immunity and Cell Growth Regulation*, 4(5):275 (1985).
Supplementary European Search Report for Application No. 05 75 5776, dated Aug. 24, 2009.
Okamoto, et al., "The nuclear acidic protein (MTI-II is a new type of nuclear-receptor coactivator," *Vitamins*, vol. 78, No. 4, p. 263, 2004.

*Primary Examiner* — Ruixiang Li
(74) *Attorney, Agent, or Firm* — Marshall, Gerstein & Borun LLP

(57) ABSTRACT

It is intended to surely and effectively inhibit the transcriptional activity of NFκB and to obtain a more effective anti-inflammatory effect. Further, it is intended to obtain an equivalent effect even if the amount used of a steroid agent is reduced.
An agent is characterized by containing MTI-II, especially a nucleic acid sequence of SEQ ID NO: 1, or a peptide of SEQ ID NO: 2. This MTI-II peptide is preferably a peptide containing at least an acidic amino acid domain (SEQ ID NO: 3). Further, a steroid agent such as triamcinolone acetonide is used concomitantly with MTI-II, especially the nucleic acid sequence of SEQ ID NO: 1 or the peptide of SEQ ID NO: 2.

18 Claims, 5 Drawing Sheets

Fig. 4

His-Tag
MA|HHHHHH|SLVPRGS|RRRQRRKKRG|LQMSEKSVEAAAELSAKDLKEKKDKVE
         TAT SEQUENCE            MTI-II SEQUENCE
EKAGRKERKKEVVEEEENGAEEEEETAEDGEDGEDDDEGDEEEEEEDEGPV
RKRTAEEEDEADPKRQKTENGASA*

NFκB TRANSCRIPTIONAL ACTIVITY INHIBITORY AGENT AND ANTI-INFLAMMATORY AGENT AND A STEROID ACTION ENHANCING AGENT

CROSS REFERENCE TO RELATED APPLICATIONS

This is the U.S. national phase of International Application No. PCT/JP05/011851 filed Jun. 28, 2005, which claims priority from Japanese Patent Application JP 2004-192160 filed Jun. 29, 2004, the entire disclosure of which is incorporated herein by reference.

TECHNICAL FIELD

The present invention relates to an NFκB transcriptional activity inhibitory agent and an anti-inflammatory agent and a steroid action enhancing agent.

BACKGROUND ART

It is known that the expression of various cytokines and cell adhesion molecules is involved in inflammatory responses. Binding the inflammatory cytokines to their specific receptors induces many lines of phosphorylation cascade within the cell cytoplasm. It is considered that these lines of phosphorylation cascade ultimately converge into activation of NFκB, which is a nuclear transcription factor, to enhance the transcriptions for inflammatory materials in the cell.

Thus, the inflammatory responses ultimately converge into the activation of NFκB. A steroid agent is used as an agent that effectively inhibits this transcriptional activity of NFκB.

Steroid agents are used as effective drugs for the treatment of intractable autoimmune hepatitis, fulminant hepatic failure and chronic hepatitis as well as liver cirrhosis and liver cancer induced by them. However, it is known that while steroid agents have a very potent effect, they also have serious side effects such as steroid ulcer, moon face, diabetes or osteoporosis. These side effects are in many cases caused in accordance with the amount used thereof. Further, the steroid agents are known to exhibit various effects on cell proliferation or sugar metabolism, other than the anti-inflammatory effect. The details of the anti-inflammatory effect of the steroid agent have not yet been completely elucidated.

On the other hand, it is known that NFκB is involved in the onset of various diseases including auto-immune diseases such as rheumatism and collagen diseases and allergy diseases such as asthma and pollen allergy, and not only with inflammatory diseases (acute and chronic hepatitis, kidney inflammation, articular inflammation and the like). Therefore, it is predicted that the inhibition of the transcriptional activity of NFκB could relieve the symptoms related to the NFκB.

Therefore, as an agent alternative to steroid agents, or as various therapeutic agents, development of a substance that inhibits the transcriptional activity of NFκB has progressed with a focus on natural extracts and synthetic substances (for example, Patent documents 1 to 3).

Further, in Patent document 4, the focus is placed particularly on p65 subunit of NFκB. Inhibiting the transcriptional activity of NFκB by using an RelA binding inhibitor that binds to this p65 subunit is described. Patent document 1: JP-A-8-319238

Patent document 2: JP-A-9-59151
Patent document 3: JP-A-11-279057
Patent document 4: JP-A-2000-224993

DISCLOSURE OF INVENTION

Problems to be Solved by the Invention

However, various natural extract components and synthetic substances do not directly affect NFκB even if they are involved in a part of the complicated intracellular mechanism or cascade, and also how they inhibit NFκB has not yet been completely elucidated. Therefore, they are not sufficient from the viewpoint of ensuring the inhibition of NFκB.

In the technique of using RelA binding inhibitor, because RelA binding inhibitor is a protein with a molecular weight of 40,000 (351 amino acids), it is difficult to incorporate the protein into the cell from outside.

On the other hand, steroid agents are still useful agents. Moreover, because they have been widely used for a long time, there is a lot of information relating to the drug efficacy thereof, and also they have advantages of good usability. Thus, even if steroid agents do have various side effects, it is expected that by controlling the amount used thereof the side effects can be suppressed while continuing the use of steroids, and more effective treatment can be carried out.

Accordingly, an object of the present invention is to provide an NFκB transcriptional activity inhibitory agent that can surely and effectively inhibit the transcriptional activity of NFκB.

Further, another object of the present invention is to provide an anti-inflammatory agent that has a more effective anti-inflammatory effect.

Another object of the present invention is to provide a steroid action enhancing agent that can effectively enhance the action of a steroid and, therefore, can reduce the amount of the steroid agent used.

Furthermore, an object of the present invention is to provide a useful pharmaceutical composition that has various applications.

Means for Solving the Problems

The NFκB transcriptional activity inhibitory agent of the present invention is characterized by comprising a nucleic acid sequence encoding MTI-II, or a peptide thereof.

The MTI-II is preferably a nucleic acid sequence of SEQ ID NO: 1 or a peptide of SEQ ID NO: 2, and is particularly preferably contains at least a peptide of SEQ ID NO: 3. Further, the MTI-II is preferably fused to a protein transduction domain.

Further, the anti-inflammatory agent of the present invention is characterized by comprising a nucleic acid sequence encoding MTI-II, or a peptide thereof.

Further, the steroid action enhancing agent of the present invention is characterized by comprising a nucleic acid sequence encoding MTI-II, or a peptide thereof.

Further, the pharmaceutical composition of the present invention comprises a nucleic acid sequence encoding MTI-II, or a peptide thereof.

Effect of the Invention

According to the present invention, the nucleic acid sequence encoding MTI-II, or a peptide thereof contained in the respective NFκB transcriptional activity inhibitory agent and the anti-inflammatory agent acts directly and in an inhibitory manner on the mechanism of transcriptional activity of NFκB in the nucleus. Therefore, the action of NFκB can be effectively and surely inhibited, and an anti-inflammatory effect can be effectively exhibited.

Further, according to the present invention, the nucleic acid sequence encoding MTI-II, or a peptide thereof increases the transcriptional activity of a steroid receptor and effectively enhances the action of a steroid, therefore, the effect of the steroid agent is enhanced and as a result, the used amount thereof can be reduced.

Further, according to the present invention, useful pharmaceutical compositions having various applications can be provided.

BRIEF DESCRIPTION OF THE DRAWINGS

FIG. 4 is a view showing a structure of His-Tag-TAT-MTI-II according to the Example of the present invention.

BEST MODE FOR CARRYING OUT THE INVENTION

Figure 1:
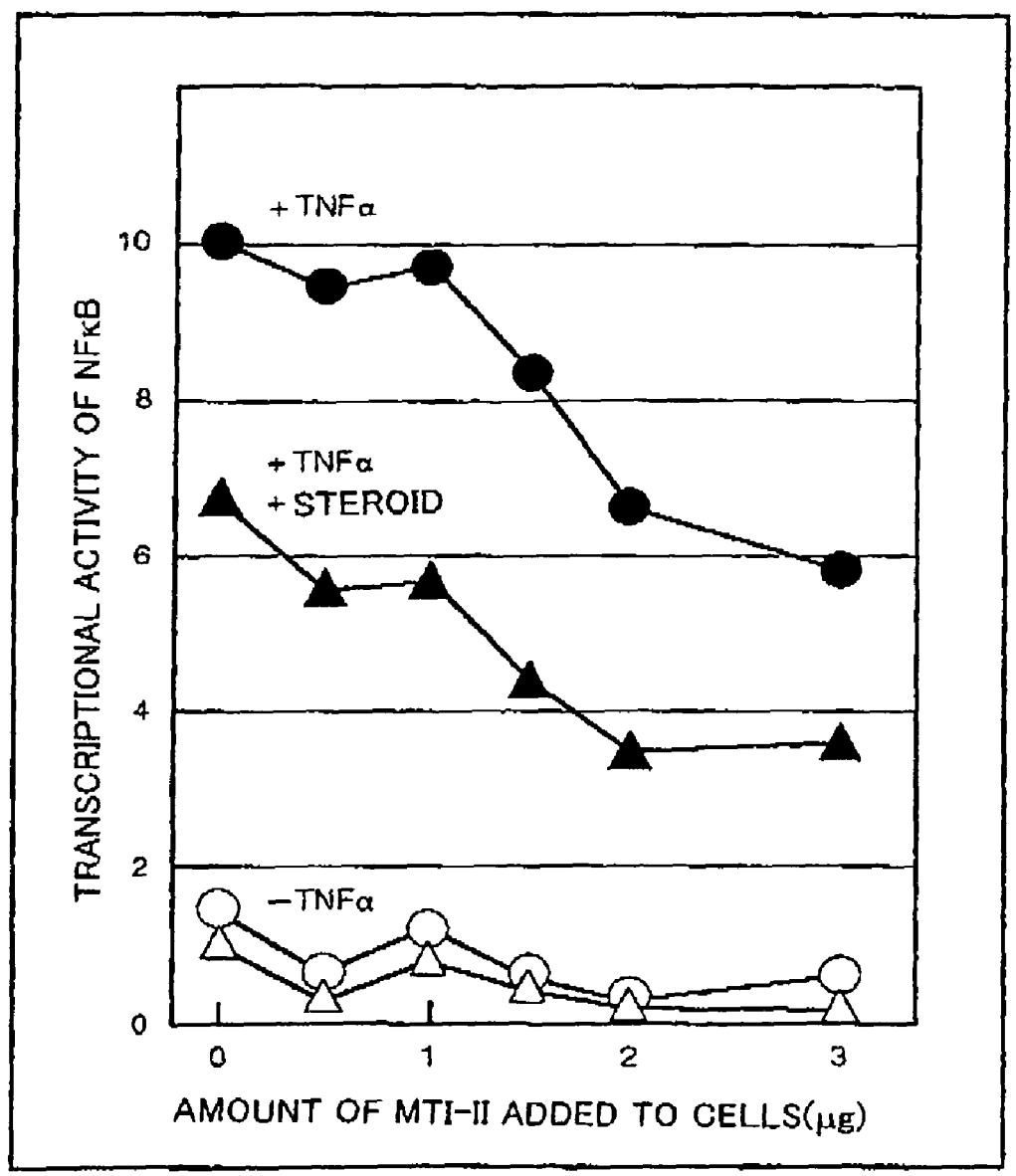
FIG. 1 is a graph showing an inhibitory effect of MTI-II, according to an Example of the present invention, on the transcriptional activity of NFκB induced by TNFα.

An NFκB transcriptional activity inhibitory agent of the present invention is characterized by comprising a nucleic acid sequence encoding MTI-II, or a peptide thereof.

MTI-II is found as an inhibitor of the nuclear binding of a steroid receptor in the rat liver (Biochem. Biophys. Res. Commun., (1982), 108, 1655-1660). After analysis of its amino acid sequence, it was confirmed that the sequence is the same as that of parathymosin (Proc. Natl. Acad. Sci., (1985), 82, 1050-1053) and that of a zinc-binding protein (J. Biol. Chem., (1886), 261, 5892-5900) (Eur. J. Biochem., (2000), 267, 155-162). The present inventors found that this MTI-II binds to a steroid receptor in the nucleus and acts on coactivators such as SRC-1 and CBP/p300 which regulate the transcriptional activity of NFκB, and then effectively inhibits the transcriptional activity of NFκB.

The MTI-II according to the present invention is preferably a nucleic acid sequence of SEQ ID NO: 1 (Gene Bank Accession No. M24398: Human parathymosin mRNA, complete cds.) or a peptide having an amino acid sequence (SEQ ID NO: 2) based on this nucleic acid sequence. However, in vivo, the methionine located at position 1 is released by modification after translation and the serine located at position 2 is modified by acetylation, whereby the MTI-II becomes a modified (acetylated) MTI-II peptide. In the present invention, this modified MTI-II peptide may be directly used.

MTI-II is a small polypeptide of a sequence composed of 102 amino acid residues and includes a thymosin homologue domain (1-31 amino acid residues), acidic amino acid domains (32-75 amino acid residues: SEQ ID NO: 3, 84-90 amino acid residues: SEQ ID NO: 4) and nuclear localization signal domains (79-81 amino acid residues: SEQ ID NO: 5, 92-96 amino acid residues: SEQ ID NO: 6). The homology between the thymosin homologue domain and thymosin is about 50% at the amino acid level. It is thought that a domain that has an inhibitory action on the transcriptional activity of NFκB in MTI-II is the acidic amino acid domains (SEQ ID NOS: 3 and 4), therefore, it is only necessary to contain at least the acidic amino acid domain represented by SEQ ID NO: 3, however, it is preferred that both domains of SEQ ID NOS: 3 and 4 (32-90 amino acid residues) and the nuclear localization signal domain (at least one of the domains of SEQ ID NOS: 5 or 6 are contained, preferably both domains) from the viewpoint of nuclear localization.

The MTI-II according to the present invention may contain addition, deletion or substitution which does not impair the activity of MTI-II.

In the case where the NFκB transcriptional activity inhibitory agent of the present invention contains the MTI-II as a nucleic acid sequence, it is only necessary that a functional MTI-II peptide can be expressed by an appropriate expression system, and it may be DNA, RNA or a nucleic acid sequence similar to them. In this case, as the expression system, an expression vector inserted with a cDNA encoding MTI-II downstream of an appropriate promoter in an appropriate vector is produced and the resulting expression vector may be introduced into a cell using a liposome or the like. As a result, a functional MTI-II can be expressed in the cell. As for a vector and a promoter that can be used for this purpose, those described below can be used as such.

The administration amount of the NFκB transcriptional activity inhibitory agent of the present invention varies depending on the age, weight, symptoms, therapeutic effect, administration method, administration site, treatment time or the like, however, in general, in terms of the nucleic acid molecule or peptide, it is orally administered at a dose of from 10 μg to 100 mg per adult human once or several times per day, or it is parenterally administered at a dose of from 1 μg to 100 mg per adult human once or several times per day. However, the administration amount varies depending on various conditions as described above, therefore, an amount smaller than the above administration amount is sufficient in some cases and an amount exceeding the above range is required in some cases.

As MTI-II according to the present invention, one obtained by purification from a naturally occurring products (a living organism or a cultured product) may be used, or one obtained in accordance with the nucleic acid sequence or amino acid sequence thereof may be used. In the case where it is obtained in accordance with the nucleic acid sequence or amino acid sequence, a peptide may be synthesized in accordance with the amino acid sequence, or it may be produced by a recombinant DNA technique using the nucleic acid sequence. In terms of the purity or from the industrial viewpoint, it is preferably produced by a recombinant DNA technique.

An expression system (host-vector system) for producing the peptide using a recombinant DNA technique includes, for example, those of bacteria, yeasts, insect cells, mammalian cells and the like.

For example, in the case where the expression is achieved in *E. coli*, a start codon (ATG) is added to the 5' terminus of a cDNA encoding a mature protein region or a proform protein region and the resulting cDNA is connected downstream of an appropriate promoter and inserted into a vector that functions in *E. coli*, whereby an expression vector is prepared.

As the promoter to be used here, for example, a trp promoter, a lac promoter, a λPL promoter, a T7 promoter and the like can be exemplified, and as the vector, for example, pBR322 pUC18, pUC19 and the like can be exemplified.

Subsequently, *E. coli* transformed with this expression vector is cultured in an appropriate medium, whereby a desired polypeptide can be obtained from the bacterial cells. Further, by using a bacterial signal peptide, it is also possible to allow a desired polypeptide to be secreted in periplasm. Further, it is also possible to produce a fusion protein with another polypeptide.

As the *E. coli* to be used here, for example, *E. coli* DH5α, *E. coli* JM109, *E. coli* HB101 strains and the like can be exemplified. As the signal peptide, for example, pelB signal peptide can be exemplified.

In the case where the expression is achieved in a mammalian cell, for example, a cDNA encoding a nucleotide sequence represented by SEQ ID NO: 1 is inserted downstream of an appropriate promoter into an appropriate vector to prepare an expression vector. Then, by using the resulting expression vector, an appropriate mammalian cell is transformed and the resulting transformant is cultured in an appropriate medium, whereby a desired peptide is secreted in the culture medium. The thus obtained peptide can be isolated and purified by a general biochemical method.

As the vector to be used here, for example, a retrovirus vector, a papillomavirus vector, a vaccinia virus vector, an SV40 vector and the like can be exemplified. As an appropriate promoter therein, for example, an SV40 promoter, an SRα promoter, an LTR promoter, a metallothionein promoter and the like can be exemplified. Further, as mammalian cells to be used here, for example, an undifferentiated human eosinophilic leukemia EOL cell line, an HeLa cell line, a CV-1 cell line, a COS-7 cell line, a CHO cell line, a mouse L cell line and the like can be exemplified.

The NFκB transcriptional activity inhibitory agent of the present invention preferably has a transduction means for promoting the transduction of MTI-II into a cell. As a result, the transduction of MTI-II in the agent of the present invention into a cell is promoted, and the transcriptional activity of NFκB can be effectively inhibited.

Such a transduction means into a cell is preferably one directly added to the MTI-II molecule, and for example, a protein transduction domain can be exemplified. In this case, the NFκB transcriptional activity inhibitory agent includes MTI-II fused to a protein transduction domain as the MTI-II molecule.

Examples of such a protein transduction domain (PTD) include any substances that can impart cell membrane permeability, and preferred examples thereof include peptides composed of 7 to 11 amino acids, for example, HIV-TAT (SEQ ID NO: 7), HSV/VP22 (SEQ ID NO: 8), ANTENNAPEDIA (SEQ ID NO: 9), polyarginine and the like can be exemplified.

The fusion site of a PTD may be any site of the N terminus or the C terminus of the MTI-II peptide. However, the action of MTI-II such as the inhibitory action on the transcriptional activity of NFκB or the inflammatory action is considered to be present in a range from the central part to the C-terminal side, and further, one of the nuclear localization signals of MTI-II is present in the C-terminal side, therefore, the PTD is preferably fused to the N-terminal side, which has less effect on these regions.

The PTD may be one fused by a direct chemical bond or via a linker molecule. In the case where a linker molecule is used, the linker molecule may be any as long as it has a bivalent chemical structure that can link two domains, and is preferably a short peptide, for example, a peptide having 1 to 20 amino acid residues, preferably 1 to 10 amino acid residues.

The MTI-II fused to a protein transduction domain may be produced by chemical synthesis of a peptide, however, it is preferably produced by a genetic engineering technique because it can be obtained easily with high purity and in a large amount by the technique. The production of such a fusion protein can be easily carried out by a person skilled in the art by the same method as described above.

As another transduction means into a cell, a liposome can be exemplified. In this case, in accordance with a standard method, MTI-II is introduced into a liposome, and then the liposome is transduced into a cell. As the liposome to be used here, any liposome can be used as long as it enables the transduction of a substance into a cell, however, it is preferably a membrane fusion liposome having a membrane fusion protein with high affinity for a cell membrane on the surface of the liposome. By this, MTI-II can be more efficiently transduced into a cell. As such a membrane fusion protein, a Sendai virus membrane fusion protein and the like can be exemplified.

Further, the NFκB transcriptional activity inhibitory agent of the present invention can contain a steroid agent in addition to MTI-II. By the simultaneous use with a steroid agent, MTI-II acts in cooperation with it, and can inhibit the transcriptional activity of NFκB more effectively.

The phrase "contain a steroid agent" is not limited to the case where MTI-II and a steroid agent are simultaneously present in the same single agent and includes the meaning of being composed of two agents, i.e., a steroid agent and MTI-II. In the case where it is composed of two agents, after the individual agents are administered separately, the agents are simultaneously present in the body, and the same effect as that of the case where it is administered as a single agent can be obtained.

As the steroid agent to be used here, generally those exhibiting a steroid action in vivo, particularly all those recognized as a steroid agent in this field (including both naturally occurring products and synthetic products), for example, those binding to a steroid receptor with high affinity and exhibiting a steroid action can be exemplified. Examples thereof include, but not limited to, synthetic steroids such as triamcinolone acetonide, dexamethasone, dexamethasone sodium phosphate, dexamethasone palmitate, betamethasone, betamethasone sodium phosphate and betamethasone acetate, and physiological steroid synthetic compounds such as hydrocortisone, fludrocortisone acetate, hydrocortisone sodium succinate and hydrocortisone sodium phosphate. With regard to these steroid agents, commercially available versions thereof can be used as they are.

The formulating amount of the steroid agent in the NFκB transcriptional activity inhibitory agent of the present invention can be determined according to the final concentration of the respective steroid agents. With regard to the concentration of the steroid agent, a concentration obtained from a standard used amount which is generally applied as the respective steroid agents can be applied as it is. In this case, because the effect of the steroid agent is enhanced by MTI-II, a higher effect than obtained from using the steroid agent of the standard used amount can be expected. Further, in order to obtain an equivalent effect to the effect obtained from using the standard used amount, the used amount of the steroid agent can be reduced. In this case, the used amount of the steroid agent can be determined according to the ratio of the effect enhanced by MTI-II, and for example, it can be determined to be one-half to one-tenth the standard used amount which is generally applied.

In the NFκB transcriptional activity inhibitory agent of the present invention, a pharmaceutically acceptable excipient and/or carrier can be further contained. The type and amount of such excipients and carriers may be appropriately selected from the known ones that are generally applied for this purpose in this field according to the dosage form of the NFκB transcriptional activity inhibitory agent which will be described below.

As the dosage form of the NFκB transcriptional activity inhibitory agent, oral administrations of a solid composition, a liquid composition and other compositions; parenteral administrations of an injection, a preparation for external use, a suppository and the like can be exemplified. As a solid composition for oral administration, a tablet, a pill, a capsule, a powder, a granule, a solution and the like can be exemplified, and further as a capsule, a soft capsule or a hard capsule can be employed. Production methods of such preparations can be carried out in accordance with a method known in this field.

Further, the NFκB transcriptional activity inhibitory agent of the present invention is preferably used as a transdermal absorption preparation that can be easily administered to the site of application. As the dosage form of such a transdermal absorption preparation, a dosage form that is commonly used as a conventional preparation for external use can be employed, and for example, it can be used as a preparation for external use in a dosage form such as a tape, a patch, a cataplasm, an ointment, a cream, a lotion, a liquid, a gel or the like. The preparation for external use in such a dosage form can be produced by a common method with the use of a general adhesive, base material and the like.

The NFκB transcriptional activity inhibitory agent of the present invention exhibits an inhibitory action on the transcriptional activity of NFκB by increasing the transcriptional activity of a steroid receptor, therefore, it has various activities corresponding to this Examples of the activities include an anti-inflammatory activity, an anti-allergic activity, an anti-autoimmune activity and the like.

With regard to the anti-inflammatory activity, the presence or absence of the activity can be confirmed in accordance with a method known in this field. The confirmation method includes, for example, determination of the degree of reduction of the transcriptional activity of NFκB against a stimulation of an inflammatory cytokine (such as TNFα) and the like.

The anti-inflammatory agent of the present invention contains a nucleic acid encoding MTI-II, or a peptide thereof. As well as the nucleic acid encoding MTI-II, or a peptide thereof, all the contents described in the NFκB transcriptional activity inhibitory agent of the present invention can also be applied to the anti-inflammatory agent of the present, invention as such. In particular, in the anti-inflammatory agent containing further the steroid agent described above, because of the simultaneous use of the steroid agent and MTI-II, an effect of MTI-II on enhancing steroid anti-inflammatory action is exhibited, whereby a higher anti-inflammatory effect can be expected.

The action of the anti-inflammatory agent of the present invention can be evaluated, as described above, by using the reduction against the stimulation of the respective inflammatory cytokines as an indicator.

The steroid action enhancing agent of the present invention contains a nucleic acid sequence encoding MTI-II, or a peptide thereof. As well as the nucleic acid sequence encoding MTI-II or a peptide MTI-II, all the contents described in the NFκB transcriptional activity inhibitory agent of the present invention can be also applied to the steroid action enhancing agent of the present invention as such.

The steroid enhanced by the steroid action enhancing agent of the present invention may be a so-called steroid agent (an exogenous steroid) or a compound having a steroid skeleton present in vivo (an endogenous steroid). In the case of using a steroid agent as a target, a steroid agent may be administered before, after or simultaneously with the application of this steroid action enhancing agent. Further, in the case of using an endogenous steroid as a target, this steroid action enhancing agent may be administered under conditions in which a target endogenous steroid is present.

Because MTI-II to be used in the present invention has a very small and simple structure, it can be easily administered and also it can directly act on NFκB, therefore, it can be effectively used. Due to this, it is not necessary to consider the diverse reactivity in the case of using a steroid agent. Accordingly, it can be effectively used as an anti-inflammatory agent.

Further, because MTI-II also has an effect on effectively relieving the symptoms of various diseases such as inflammatory diseases (acute and chronic hepatitis, kidney inflammation, articular inflammation and the like), autoimmune diseases such as rheumatism and collagen diseases and allergy diseases such as asthma and pollen allergy related to the inhibition of the transcriptional activity of NFκB without being limited to the anti-inflammatory agent, MTI-II can be used as various drug agents for these symptoms. Accordingly, the pharmaceutical composition of the present invention containing a nucleic acid sequence encoding MTI-II, or a peptide thereof has an action as such various drug agents and can be widely used.

Further, MTI-II is expressed in the heart, liver and kidney in a large amount, therefore, by administering or delivering any of the various agents and pharmaceutical compositions of the present invention specifically to these tissues, a more potent effect can be expected. Further, there is a difference in the expression amount among tissues, therefore, by causing the action of MTI-II to be expressed strongly in a tissue with less MTI-II, a high effect can be expected.

The antisense sequence of this MTI-II can be used for regulating the level of the MTI-II protein in a cell. In this case, by a method in which a part or the whole of the nucleic acid sequence encoding MTI-II is inserted into the vector described above in the antisense direction, a method in which DNA or double-stranded RNA connected to a U6 promoter upstream of the 5' side is injected into a cell or the like, the antisense sequence can be easily prepared and utilized in a cell.

Hereinafter, Examples of the present invention will be described, however, the present invention is not restricted to these. Unless otherwise specified, the percentages in the Examples are percentages by weight (mass).

Example 1

MTI-II Peptide Administration Experiment

MTI-II of SEQ ID NO: 1 (Gene Bank Accession No. M24398) was purified in accordance with the purification method described in the document (Eur. J. Biochem., (2000), 267, 155-162). It was dissolved in physiological saline at a concentration of 1.0 mg/ml and intraperitoneally administered to 5 male (an average body weight of 28.4 g) and 5 female (an average body weight of 25.0 g) ICR mice at 5 weeks of age at 10 mg/kg of body weight. As a control, physiological saline was administered to 2 male and 2 female ICR mice of the same age. After the administration, the presence or absence of behavioral anomaly was observed for 24 hours (every 8 hours, 3 times in total). At 24 hours after the administration, they were sacrificed and autopsy was carried out and the swelling of the liver, kidney, spleen, small intestine, large intestine and thymus and the swelling of the blood vessels in the abdominal cavity were observed by the naked eye. As a result, behavioral anomaly and the swelling of the liver, kidney, spleen, small intestine, large intestine, thymus and blood vessels were not observed in all specimens.

Example 2

DNA Construction

An MTI-II expression vector (pTri-MTI) used in DNA transfection was constructed as follows.

A cDNA of MTI-II (SEQ ID NO: 1: Gene Bank Accession No. M24398) was amplified from mRNA obtained from HeLa cells by the RT-PCR method. The amplified cDNA of MTI-II was inserted into the NcoI-HindIII site of pTriEx-4 vector (Novagen, catalog number: 70824-3), whereby the MTI-II expression vector (pTri-MTI) was constructed. The expression vector (pTri-GR) of a steroid receptor (GR) was constructed by inserting a GR cDNA (Gene Bank Accession No. M14053) amplified from rat mRNA by the RT-PCR method into the BglII-NotI site of pTriEx-4 vector.

A plasmid for a negative control (pTri-NC) was constructed by self-ligation after pTriEx-4 vector was digested with XcmI and EcoRI. An NFκB-dependent luciferase expression plasmid (NFκB-Luc) was purchased from Clontech (catalog number: 6053-1) and a *Renilla* Luciferase expression plasmid (pRL-TK) for an intrinsic control was purchased from Promega (catalog number: E2241).

Example 3

DNA Transfection

The transfection of each DNA was carried out based upon the transfection protocol of TransFast (product name, catalog number: E2431) of Promega. This will be briefly explained below.

COS-7 cells were plated into a 6-well plate (Falcon, catalog number: 35-3046) at 3.5 to 3.8×10$^5$ cells per well and cultured in a DMEM supplemented with 10% 56° C.-inactivated FBS (fetal bovine serum; HyClone, catalog number: SH30070.03) under the conditions of 5% $CO_2$ and 37° C. After 18 hours, the medium was replaced with a DMEM containing charcoal-dextran treated (C/D treatment) FBS (C/D-FBS, HyClone, catalog number: SH30068.03).

Each of the plasmids constructed in Example 2 was mixed as shown in Table 1 and each sample was prepared to be 4.12 μg and each was mixed with TransFast (product name) reagent (12.3 μl) and the mixture was incubated for 10 to 15 minutes.

After the medium in each well was replaced, each plasmid DNA was added to the respective wells according to the amount shown in Table 1 and incubation was carried out for 1 hour, thus each DNA was transfected into COS-7 cells. The transfection efficiency was 34%.

TABLE 1

| No. | NFκB-Luc μg | pRL-TK μg | pTri-GR μg | pTri-NC μg | pTri-MTI μg |
|---|---|---|---|---|---|
| 1 | 1.0 | 0.02 | 0.1 | 3.0 | 0.0 |
| 2 | 1.0 | 0.02 | 0.1 | 2.5 | 0.5 |

TABLE 1-continued

| No. | NFκB-Luc μg | pRL-TK μg | pTri-GR μg | pTri-NC μg | pTri-MTI μg |
|---|---|---|---|---|---|
| 3 | 1.0 | 0.02 | 0.1 | 2.0 | 1.0 |
| 4 | 1.0 | 0.02 | 0.1 | 1.5 | 1.5 |
| 5 | 1.0 | 0.02 | 0.1 | 1.0 | 2.0 |
| 6 | 1.0 | 0.02 | 0.1 | 0.0 | 3.0 |

Example 4

Luciferase Assay

To the cells into which DNA was transfected as described above, after 24 hours, an inflammatory cytokine (TNFα, Sigma) at a final concentration of 1 ng/ml and a steroid agent (triamcinolone acetonide: TA, Sigma) at a final concentration of 120 nM were added. Further, after an additional 24 hours, luciferase activities in the cells were assayed using Dual Luciferase Assay System (Promega) by a luminometer (Turner BioSystems TD-20/20, Promega). The results are shown in FIG. 1, In FIG. 1, the luciferase activities indicating the transcriptional activity of NFκB is indicated on the vertical axis. The closed circles show the case where only TNFα was added, the closed triangles show the case where both TNFα and TA were added, the open triangles show the case where only TA was added and the open circles show the case where neither of TNFα nor TA was added, respectively.

As shown in FIG. 1, when only TNFα was added (closed circles) under the condition where MTI-II was not contained (MTI-II was 0 μg), the luciferase activity about 10 times higher than that of the case where TNFα was not added was observed. Thus, the transcriptional activity of NFκB was increased by the addition of TNFα. It was also shown that the transcriptional activity of NFκB was inhibited by the addition of the steroid agent in addition to TNFα.

Contrary to this, it was shown that when MTI-II was expressed, the transcriptional activity of NFκB was inhibited depending on the amount of MTI-II. In particular, when MTI-II expression vector was added at 1 μg or more, the NFκB transcriptional activity was significantly inhibited. When MTI-II expression vector was added at 2 μg or more, the inhibition by MTI-II was more effective than that by steroid agent.

Further, by the simultaneous use of MTI-II and the steroid agent, the NFκB transcriptional activity could be inhibited further more. This indicates that the effect of the steroid agent is enhanced by MTI-II.

Therefore, it is clear that MTI-II itself has an effective inhibitory effect on NFκB transcriptional activity. Further, it is also obvious that the inhibitory effect can be enhanced by the simultaneous use with a steroid agent. Thus, by using the NFκB transcriptional activity inhibitory agent and the anti-inflammatory agent of the present invention containing MTI-II, the transcriptional activity of NFκB can be effectively and surely inhibited, and an anti-inflammatory effect can also be obtained. Further, because the effect of a steroid agent can be enhanced, an equivalent effect can be obtained even if a reduced amount of a steroid agent is used.

Example 5

Inhibitory Effect of MTI-II on Transcriptional Activity of NFκB in the Presence of a Coactivator Then, in order to confirm the action site of MTI-II, the effect of MTI-II was investigated when a coactivator p300, which acts on the transcriptional activity of NFκB, was expressed.

A coactivator p300 expression plasmid (pCMVβ-p300) was purchased from Upstate. DNA transfection was carried out in the same manner as in Example 3 except that the amount of DNA was each 2.0 μg and the amount of pTri-NC or pTri-MTI was 1.0 μg. The NFκB transcriptional activity assay was carried out in the same manner as in Example 4. The results are shown in FIG. 2.

Figure 2:
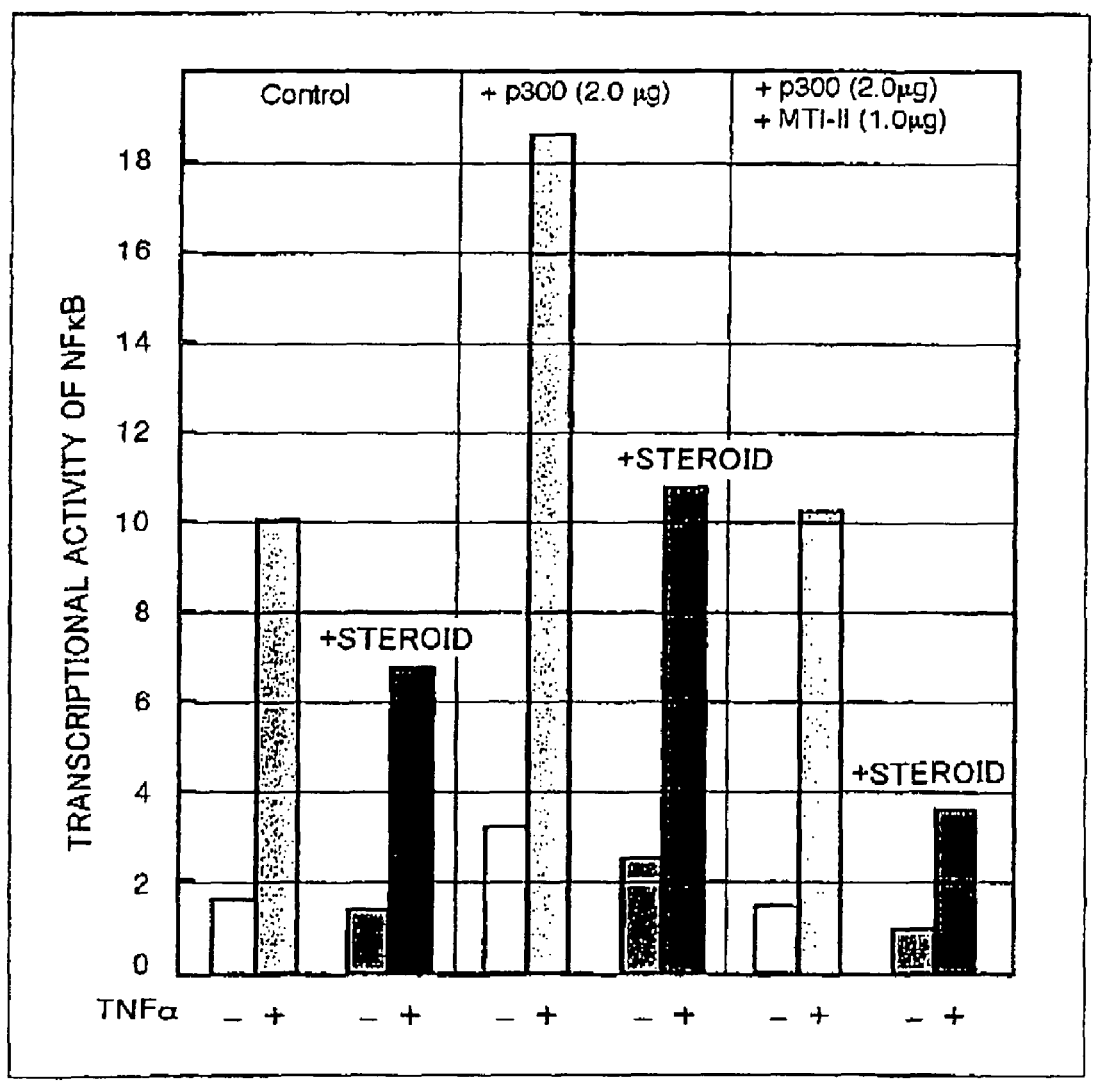
FIG. 2 is a graph showing an inhibitory effect of MTI-II according to the Example of the present invention on the transcriptional activity of NFκB induced by TNFα in the presence of a coactivator.

As shown in FIG. 2, when p300 was expressed (FIG. 2, center), the transcriptional activity of NFκB became significantly high by the addition of TNFα. In this case, the transcriptional activity of NFκB could be inhibited to about half by the addition of the steroid agent (FIG. 2, center).

On the other hand, in the case where MTI-II was expressed together with p300 or the steroid agent was further added, the transcriptional activity of NFκB was inhibited to about half or more compared with the case where MTI-II was not expressed in each case (FIG. 2, right) In particular, in the case where it is used together with the steroid agent, even if the coactivator was expressed, the transcriptional activity of NFκB could be inhibited to about half of that in the absence of the coactivator (FIG. 2, left).

Therefore, MTI-II could inhibit the transcriptional activity of NFκB surely and effectively even in the presence of the coactivator.

Example 6

Inhibitory Effect of Acidic Amino Acid Domain on the Transcriptional Activity of NFκB Subsequently, which domain among amino acids of MTI-II is involved in the inhibitory effect of MTI-II on the transcriptional activity of NFκB was examined.

Figure 3:
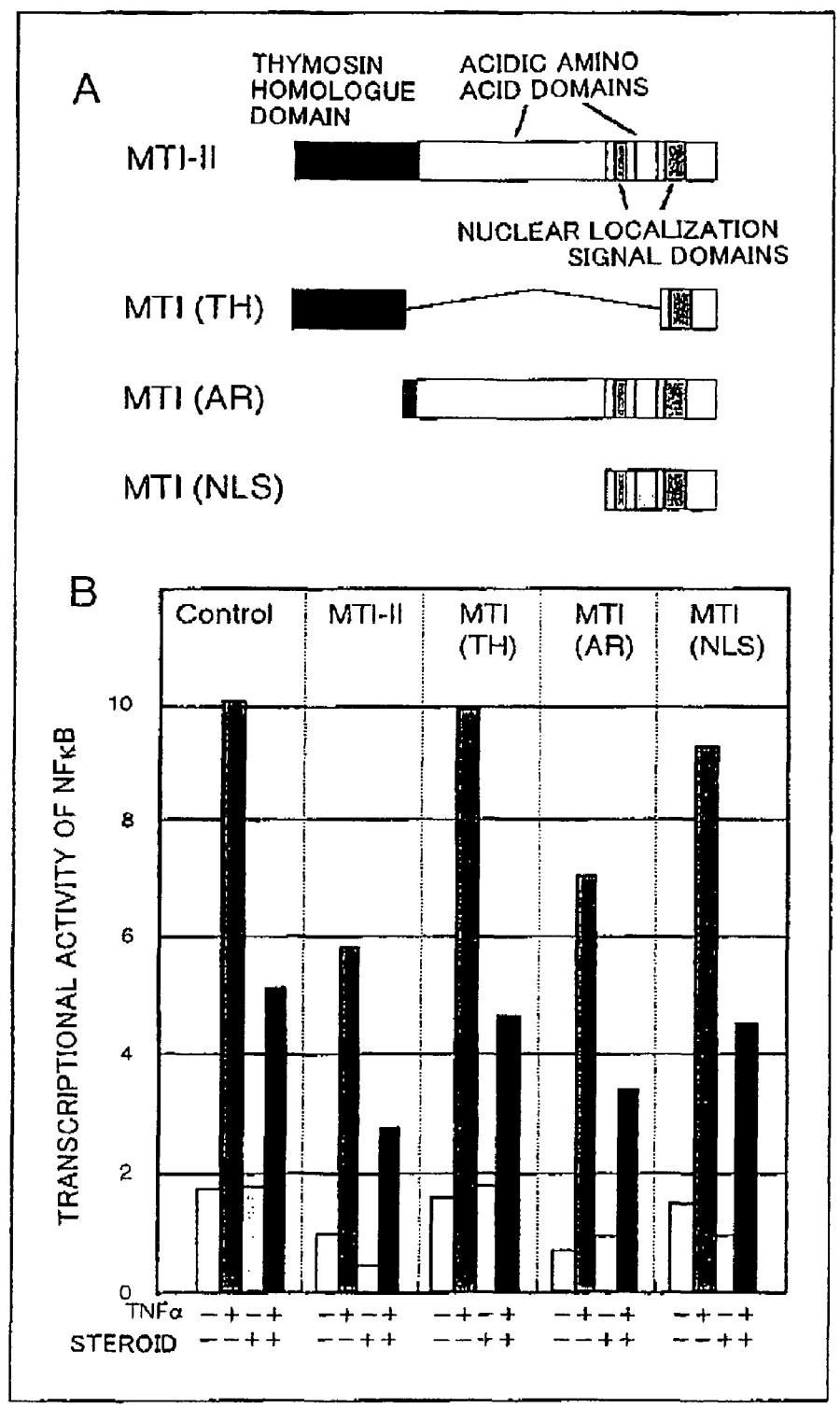
FIG. 3A is a schematic view showing the various MTI-II mutant vectors prepared for the purpose of examining an effect of MTI-II according to the Example of the present invention.
FIG. 3B is a graph showing an inhibitory effect on the transcriptional activity of NFκB induced by TNFα using the various MTI-II mutant vectors shown in FIG. 3A.

As shown in FIG. 3A, the amino acid domain of MTI-II includes a thymosin homologue domain, acidic amino acid domains (SEQ ID NOS: 3 and 4) and nuclear localization signal domains (SEQ ID NOS: 5 and 6). Therefore, vectors that express respectively in cells, a mutant [MTI(TH)] in which the thymosin homologue domain at the N-terminal side and the nuclear localization signal domain (SEQ ID NO: 6) at the C-terminal side are contained and the acidic amino acid domains are deleted, a mutant [MTI(AR)] in which the acidic amino acid domains (SEQ ID NOS: 3 and 4) are contained and the thymosin homologue domain at the N-terminal side is deleted, and a mutant [MTI(NLS)] in which the nuclear localization signal domains (SEQ ID NOS: 5 and 6) are contained and the thymosin homologue domain at the N-terminal side and the acidic amino acid domain in the central area (SEQ ID NO: 3) are deleted were prepared.

The vector DNA (3.0 μg) for each mutant and an NFκB-dependent luciferase reporter plasmid (1.0 μg) were transfected into COS-7 cells and luciferase activities in the cells were assayed in the same manner as in Examples 3 and 4. The results are shown in FIG. 3B.

As shown in FIG. 3B, in both of the case where only TNFα was added and the case where the steroid agent was concomitantly used, an inhibitory effect on the transcriptional activity of NFκB was greater in MTI(AR) compared with the both cases of MTI(TH) and MTI(NLS). Therefore, it was clear that in MTI-II, the acidic amino acid domain contributes to the inhibitory effect on the transcriptional activity of NFκB.

Accordingly, it was clear that in the case where MTI-II is used, even if the thymosin homologue domain is not contained, an inhibitory effect on the transcriptional activity of NFκB is obtained.

Example 7

Synthesis of TAT-MTI-II Fusion Protein

A His-tag-TAT-MTI-II fusion protein was obtained as follows.

A cDNA of MTI-IT was inserted into the PstI-HindIII site of pTriEx-4 vector to construct a His-tag-MTI-II expression vector. Then, into the XcmI-PstI site of this expression vector, synthetic DNA (SEQ ID NO: 10: CTCTGGTC-CCCCGGGGCAGCCGTCGTCGT-CAACGTCGTAAAAAACGTGGTCTGCA) containing a TAT cDNA sequence was inserted. This His-taq-TAT-MTI-II expression vector was transfected into E. coli (Rosetta 2 pLacI cell, Novagen), and a His-tag-TAT-MTI-II protein was expressed in a large amount in the presence of IPTG. After E. coli was lysed using an E. coli expressed protein extraction reagent BugBuster (Novagen), and purification was carried out to electrophoretic homogeneity using an affinity column (Clontech) for His-tag and an anion exchanger (MonoQ column, Amersham Biosciences) and a cation exchanger (MonoS column, Amersham Biosciences). Therefore, a His-tag-TAT-MTI-II fusion protein (His-tag-TAT-MTI-II) was obtained (SEQ ID NO: 11, see FIG. 4).

Example 8

Transduction of TAT-MTI-II Protein into Cell

HeLa cells were plated into a 6-well plate at $2.0 \times 10^5$ cells per well and cultured in a DMEM (HyClone) supplemented with 10% FBS (fetal bovine serum) for 18 hours. Thereafter, the medium was replaced with a medium containing charcoal-dextran treated (C/D treatment) FBS (C/D-FBS). Further, after an additional 24 hours, each plasmid DNA blended in accordance with the amount shown in the following Table 2 was added to the respective wells, and these HeLa cells were transfected with NFκB-Luc gene.

TABLE 2

| 6-well No. | NFκB-Luc μg | Tfx-20 μl | medium ml |
|---|---|---|---|
| 1 | 1.25 | 3.8 | 1 |
| 2 | 1.25 | 3.8 | 1 |
| 3 | 1.25 | 3.8 | 1 |
| 4 | 1.25 | 3.8 | 1 |
| 5 | 1.25 | 3.8 | 1 |
| 6 | 1.25 | 3.8 | 1 |
| | 7.50 | 22.5 | 6 |

At 24 hours after the transfection, to the HeLa cells in each well, the His-tag-TAT-MTI-II fusion protein prepared in Example 7 was added according to the amount shown in Table 3, and 6 hours thereafter, an inflammatory cytokine (TNFα, Sigma) was further added thereto in an amount to give a concentration of 1 ng/ml. After 24 hours, in the same manner as in Example 4, luciferase activities in the cells were assayed using Dual Luciferase Assay System (Promega). The results are shown in FIG. 4.

TABLE 3

| 6-well No. | TAT-MTI μg | medium ml |
|---|---|---|
| 1 | 0 | 1 |
| 2 | 0 | 1 |
| 3 | 30 | 1 |

TABLE 3-continued

| 6-well No. | TAT-MTI μg | medium ml |
|---|---|---|
| 4 | 60 | 1 |
| 5 | 150 | 1 |
| 6 | 300 | 1 |

Figure 5:
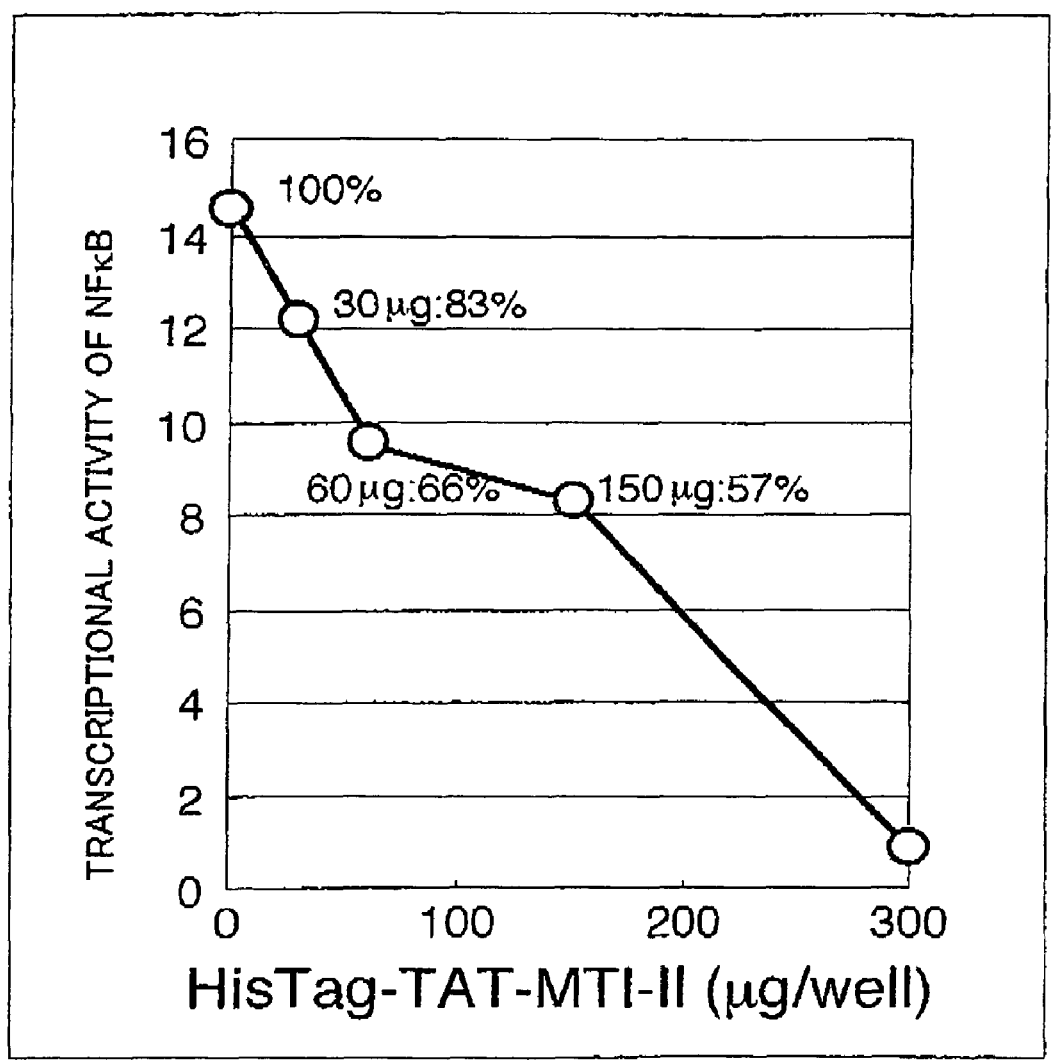
FIG. 5 is a graph showing an inhibitory effect of His-Tag-TAT-MTI-II according to the Example of the present invention on the transcriptional activity of NFκB induced by TNFα.

As shown in FIG. 5, in the case where His-tag-TAT-MTI-II was added along with TNFα, the transcriptional activity of NFκB was inhibited depending on the amount of TAT-MTI-II. This indicates that by the fusion with TAT as a protein transduction domain, the MTI-II molecule was efficiently transported into a cell and inhibited the transcriptional activity of NFκB. Accordingly, it was clear that MTI-II fused with the protein transduction domain is efficiently incorporated into a cell and can exhibit the effect of the present invention.

Example 9

For primary sensitization, ovalbumin (OVA)+Freund's complete adjuvant (FCA) was intradermally injected once in the dorsal area of three New Zealand White rabbits. After 2 weeks, for secondary sensitization, OVA+FCA was intradermally administered once in the dorsal area. Further, for challenge administration, at 5 days after the secondary sensitization, OVA was administered once into the right knee joint. A His-tag-TAT-MTI-II solution (at 0.4 mg/ml in PBS solution) was administered into the right knee joint every other day starting from one day before the challenge administration of OVA. Incidentally, during 5 days from the next day of the challenge administration of OVA, the His-tag-TAT-MTI-II solution was administered once daily. The administration period was 14 days (number of administration: 10 times in total), and in a control group, PBS was administered into the right knee joint. An anti-inflammatory action was examined based on the blood sedimentation rate measurement and the pathological specimens of both knee joints. These results indicate an anti-inflammatory effect in the group administered with the TAT-MTI-II solution.

As is shown in these Examples, by using MTI-II, at least an acidic amino acid domain thereof, the transcriptional activity of NFκB can be surely and effectively inhibited. This effect can be also obtained by administering a peptide thereof in the same manner as DNA. Accordingly, the NFκB transcriptional activity inhibitory agent and the anti-inflammatory agent of the present invention containing MTI-II can inhibit the transcriptional activity of NFκB surely and effectively, and further they inhibit an inflammatory response and can alleviate other symptoms related to NFκB.

Further, by the simultaneous use with a steroid agent, the action of the steroid agent is enhanced, therefore, the amount of a steroid agent to be used is reduced and an equivalent effect can be achieved.

SEQUENCE LISTING

```
<160> NUMBER OF SEQ ID NOS: 11

<210> SEQ ID NO 1
<211> LENGTH: 1109
<212> TYPE: DNA
<213> ORGANISM: Homo sapiens
<220> FEATURE:
<221> NAME/KEY: CDS
<222> LOCATION: (301)..(609)

<400> SEQUENCE: 1
ggcggcgacg gatcgagctc accgcgccga gcgcgccggc accgcctgca ccgcccttcc      60
gcccgccctc cggacggccg cagcctgcgg tctccgtcca gacccacccc cgccccaccc     120
cgcgcgcctc tgccgcctct tccagagacc cagcttgccg agcggccgcc gctgccgtgt     180
cgccgccgcc gccgccaccg cgccaggttc cggccgcggc caccctccgc cgtccagggc     240
ctctccgtct cggccccggg accccgcctc cccgccagcc ccgccccgg ccccggcacc      300 atg tcg gag aag agc gtg gag gca gcg gcc gag cta agc gcc aag gac      348
Met Ser Glu Lys Ser Val Glu Ala Ala Ala Glu Leu Ser Ala Lys Asp
1               5                   10                  15 ctg aag gaa aag aag gac aag gtg gag gag aag gct ggc cgg aaa gaa      396
Leu Lys Glu Lys Lys Asp Lys Val Glu Glu Lys Ala Gly Arg Lys Glu
            20                  25                  30 cgg aag aaa gaa gta gtg gag gag gag gag aat gga gct gag gag gag      444
Arg Lys Lys Glu Val Val Glu Glu Glu Glu Asn Gly Ala Glu Glu Glu
        35                  40                  45 gaa gaa gaa act gct gag gat gga gag gat gat gat gaa gga gac gaa      492
Glu Glu Glu Thr Ala Glu Asp Gly Glu Asp Asp Asp Glu Gly Asp Glu
    50                  55                  60 gaa gat gag gag gaa gag gag gag gag gat gaa ggc ccc gtg cgg aag      540
Glu Asp Glu Glu Glu Glu Glu Glu Glu Asp Glu Gly Pro Val Arg Lys
65                  70                  75                  80
```

```
aga act gct gaa gag gag gat gaa gcg gat ccc aag agg cag aag aca      588
Arg Thr Ala Glu Glu Glu Asp Glu Ala Asp Pro Lys Arg Gln Lys Thr
            85                  90                  95 gaa aac ggg gcg tcg gct tga cgcctgccaa caggctgggt tgggaggcct         639
Glu Asn Gly Ala Ser Ala
            100 ctctgggctg gaggtggggg tgggggcagc caagtccagc cactcttcac ctggctccct    699 gctctgggcc ctgcaccgag agctgccacc ctcttctttc tccccagcct tctcatttcc    759 gcctctccag acactgcgcc ctccaccctc actctgccat tgttccacct cctgacctgc    819 tccatctgag ctctccagct ggcccccaat tgcctcctc tctctttgct ctctttctcc     879 ctcccctacc agcctcattc ttctccggta gcctctccca cctaacctct gcatccccca    939 gcgtcatgtc ctgccccatc cctatcctgc ctgatccctg gatctccctc agatcccctc    999 ttctcagaca gcgccaggcc ggggtggggc cggggttgcc gagccccaca gctgccccc    1059 tcccctccct ttttgtataa tttaataaag aaatggtcgc gcttctgttt               1109

<210> SEQ ID NO 2
<211> LENGTH: 102
<212> TYPE: PRT
<213> ORGANISM: Homo sapiens

<400> SEQUENCE: 2

Met Ser Glu Lys Ser Val Glu Ala Ala Ala Glu Leu Ser Ala Lys Asp
1               5                   10                  15

Leu Lys Glu Lys Lys Asp Lys Val Glu Glu Lys Ala Gly Arg Lys Glu
            20                  25                  30

Arg Lys Lys Glu Val Val Glu Glu Glu Asn Gly Ala Glu Glu Glu
        35                  40                  45

Glu Glu Glu Thr Ala Glu Asp Gly Glu Asp Asp Asp Glu Gly Asp Glu
    50                  55                  60

Glu Asp Glu Glu Glu Glu Glu Glu Asp Glu Gly Pro Val Arg Lys
65                  70                  75                  80

Arg Thr Ala Glu Glu Glu Asp Glu Ala Asp Pro Lys Arg Gln Lys Thr
            85                  90                  95

Glu Asn Gly Ala Ser Ala
            100

<210> SEQ ID NO 3
<211> LENGTH: 44
<212> TYPE: PRT
<213> ORGANISM: Homo sapiens

<400> SEQUENCE: 3

Glu Arg Lys Lys Glu Val Val Glu Glu Glu Asn Gly Ala Glu Glu Glu
1               5                   10                  15

Glu Glu Glu Thr Ala Glu Asp Gly Glu Asp Asp Asp Glu Gly Asp
            20                  25                  30

Glu Glu Asp Glu Glu Glu Glu Glu Glu Asp Glu
        35                  40

<210> SEQ ID NO 4
<211> LENGTH: 7
<212> TYPE: PRT
<213> ORGANISM: Homo sapiens

<400> SEQUENCE: 4

Glu Glu Glu Asp Glu Ala Asp
1               5
```

```
<210> SEQ ID NO 5
<211> LENGTH: 3
<212> TYPE: PRT
<213> ORGANISM: Homo sapiens

<400> SEQUENCE: 5

Arg Lys Arg
1

<210> SEQ ID NO 6
<211> LENGTH: 5
<212> TYPE: PRT
<213> ORGANISM: Homo sapiens

<400> SEQUENCE: 6

Lys Arg Gln Lys Thr
1               5

<210> SEQ ID NO 7
<211> LENGTH: 10
<212> TYPE: PRT
<213> ORGANISM: Artificial
<220> FEATURE:
<223> OTHER INFORMATION: TAT

<400> SEQUENCE: 7

Arg Arg Arg Gln Arg Arg Lys Lys Arg Gly
1               5                   10

<210> SEQ ID NO 8
<211> LENGTH: 34
<212> TYPE: PRT
<213> ORGANISM: Artificial
<220> FEATURE:
<223> OTHER INFORMATION: HSV/VP22

<400> SEQUENCE: 8

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 9
<211> LENGTH: 17
<212> TYPE: PRT
<213> ORGANISM: Artificial
<220> FEATURE:
<223> OTHER INFORMATION: ANTENNAPEDIA

<400> SEQUENCE: 9

Arg Gln Ile Lys Ile Lys Trp Pro Gln Asn Arg Arg Met Lys Trp Lys
1               5                   10                  15

Lys

<210> SEQ ID NO 10
<211> LENGTH: 55
<212> TYPE: DNA
<213> ORGANISM: Artificial
<220> FEATURE:
<223> OTHER INFORMATION: TAT cDNA insert

<400> SEQUENCE: 10
ctctggtccc ccggggcagc cgtcgtcgtc aacgtcgtaa aaaacgtggt ctgca        55
```

```
<210> SEQ ID NO 11
<211> LENGTH: 129
<212> TYPE: PRT
<213> ORGANISM: Artificial
<220> FEATURE:
<223> OTHER INFORMATION: HisTag-TAT-MTI-II

<400> SEQUENCE: 11

Met Ala His His His His His His Ser Leu Val Pro Arg Gly Ser Arg
1               5                   10                  15

Arg Arg Gln Arg Arg Lys Lys Arg Gly Leu Gln Met Ser Glu Lys Ser
            20                  25                  30

Val Glu Ala Ala Ala Glu Leu Ser Ala Lys Asp Leu Lys Glu Lys Lys
        35                  40                  45

Asp Lys Val Glu Glu Lys Ala Gly Arg Lys Glu Arg Lys Lys Glu Val
    50                  55                  60

Val Glu Glu Glu Asn Gly Ala Glu Glu Glu Glu Glu Thr Ala
65                  70                  75                  80

UNITED STATES PATENT AND TRADEMARK OFFICE
CERTIFICATE OF CORRECTION

| | | |
|---|---|---|
| PATENT NO. | : 7,932,226 B2 | |
| APPLICATION NO. | : 11/631202 | |
| DATED | : April 26, 2011 | |
| INVENTOR(S) | : Kazuki Okamoto et al. | |

It is certified that error appears in the above-identified patent and that said Letters Patent is hereby corrected as shown below:

Column 19, lines 41-46: "group consisting of a polypeptide of SEQ ID NO: 3 or a combination of a polypeptide of SEQ ID NO: 3 and a polypeptide of SEQ ID NO: 4, and wherein the nuclear localization signal domain is selected from the group consisting of a polypeptide of SEQ ID NO: 5, a polypeptide of SEQ ID NO: 6 or a polypeptide consisting of"

should be:

"group consisting of a polypeptide of SEQ ID NO: 3 and a combination of a polypeptide of SEQ ID NO: 3 and a polypeptide of SEQ ID NO: 4, and wherein the nuclear localization signal domain is selected from the group consisting of a polypeptide of SEQ ID NO: 5, a polypeptide of SEQ ID NO: 6 and a polypeptide consisting of"

Column 20, lines 40-45: "group consisting of a polypeptide of SEQ ID NO: 3 or a combination of a polypeptide of SEQ ID NO: 3 and a polypeptide of SEQ ID NO: 4, and wherein the nuclear localization signal domain is selected from the group consisting of a polypeptide of SEQ ID NO: 5, a polypeptide of SEQ ID NO: 6 or a polypeptide consisting of"

should be:

"group consisting of a polypeptide of SEQ ID NO: 3 and a combination of a polypeptide of SEQ ID NO: 3 and a polypeptide of SEQ ID NO: 4, and wherein the nuclear localization signal domain is selected from the group consisting of a polypeptide of SEQ ID NO: 5, a polypeptide of SEQ ID NO: 6 and a polypeptide consisting of"

Signed and Sealed this
Third Day of January, 2012

David J. Kappos
*Director of the United States Patent and Trademark Office*